United States Patent
Minogue et al.

(10) Patent No.: US 8,209,030 B2
(45) Date of Patent: Jun. 26, 2012

(54) APPARATUS FOR APPLYING ELECTRICAL CURRENT TO A USER'S LEG MUSCLES

(75) Inventors: Conor Minogue, Kinvara (IE); Louis Crowe, Galway (IE); Leonie Heskin, Galway (IE)

(73) Assignee: Bio Medical Research, Galway (IE)

( * ) Notice: Subject to any disclaimer, the term of this patent is extended or adjusted under 35 U.S.C. 154(b) by 0 days.

(21) Appl. No.: 13/102,668

(22) Filed: May 6, 2011

(65) Prior Publication Data

US 2011/0208266 A1    Aug. 25, 2011

Related U.S. Application Data

(63) Continuation of application No. 10/555,732, filed as application No. PCT/IB2004/001878 on May 7, 2004, now Pat. No. 7,957,816.

(30) Foreign Application Priority Data

May 7, 2003 (GB) .................................. 0310414.8

(51) Int. Cl.
*A61N 1/04* (2006.01)
(52) U.S. Cl. ............. 607/115; 607/45; 607/46; 607/116
(58) Field of Classification Search .............. 607/45–46, 607/115–116
See application file for complete search history.

(56) References Cited

U.S. PATENT DOCUMENTS

| | | | |
|---|---|---|---|
| 4,729,377 A | 3/1988 | Church et al. | |
| 6,341,237 B1 * | 1/2002 | Hurtado | 607/148 |
| 2003/0060740 A1 | 3/2003 | Faghri | |
| 2003/0088294 A1 * | 5/2003 | Gesotti | 607/45 |

FOREIGN PATENT DOCUMENTS

WO    WO 03/006106    1/2003

* cited by examiner

*Primary Examiner* — Niketa Patel
*Assistant Examiner* — Rex R Holmes
(74) *Attorney, Agent, or Firm* — Drinker, Biddle & Reath, LLP

(57) ABSTRACT

The invention relates to apparatus for applying electrical current to the quadriceps muscle. The apparatus is in the form of a garment (to be worn on a user's thigh) having a integrated programmable stimulation device including integral electronics, LCD display, user controls and a battery. To ensure accurate and repeatable positioning of the garment, it is shaped such that it locates above the patella. Furthermore, reference lines are provided on the skin facing surface of the garment to assist the user in the accurate placement of skin engaging electrodes. In combination, the features of the invention provides a safe and convenient means of electrically stimulating the quadriceps muscle irrespective of patient size whilst minimizing the opportunity for error. Moreover, the invention dispenses with the need to employ a skilled clinician to individually place each electrode.

23 Claims, 6 Drawing Sheets

APPARATUS FOR APPLYING ELECTRICAL CURRENT TO A USER'S LEG MUSCLES

CROSS-REFERENCE TO RELATED APPLICATIONS

This application is a continuation of and claims the benefit of U.S. patent application Ser. No. 10/555,732 filed Nov. 27, 2006, entitled "APPARATUS FOR APPLYING ELECTRICAL CURRENT TO THE NEUROMUSCULAR SYSTEM," now U.S. Pat. 7,957,816, which is a U.S. National Stage of PCT International Patent Application No. PCT/IB2004/001878, filed May 7, 2004, which is entitled to priority under 35 U.S.C. §119(e) to G.B. application number 0310414.8 filed May 7, 2003 all of which are hereby incorporated by reference in their entirety herein.

The present invention relates to apparatus for applying electrical current to muscles, particularly, but not exclusively, to the quadriceps muscle.

Electrical stimulation of the quadriceps muscle is well known. The quadriceps is the most important muscle to be rehabilitated after an operation on the knee. It is the strongest extensor of the knee and improving the force of its contraction after surgery consequently aids rehabilitation of the other muscles involved in ambulation.

The vastus medialis component of the quadriceps stabilises the patella in the early stages of walking. After knee surgery, not only can there be a reflex inhibition of this muscle but there can also be a temporary disruption of the joint receptor activity which interferes with the patients proprioceptive feedback. Therefore the quadriceps muscle needs additional assistance in overcoming this inhibition and early rehabilitation to aid stability.

Although the quadriceps is a large muscle in the front of the thigh, the knowledge of a clinical professional is required in order to accurately position appropriately sized electrodes according to patient size to thus ensure effective electrical stimulation. The professional must ensure that the correct channels from a stimulator unit are connected to correct electrodes on the right or left leg. Whilst previous attempts to produce a fail-safe garment for electrode application to the body have succeeded in providing more convenient methods of electrode application compared to traditional lead-wired systems, the assistance of a professional has still been required in the initial set-up stage.

A further problem exists in terms of repeatability in user application of the garment. This is often inadequate since slight shifts in the position of the electrode placement from day to day can change the effectiveness of the stimulation, especially if the garment is placed over a moving joint.

Many muscle groups have a symmetrical group on the other side of the body across the coronal plane. These muscle groups are mirror images of each other and so the electrode placement should take account of this. This has been achieved in certain garment designs before by producing a mirror image garment or by turning the existing garment inside out. Where a stimulator unit and wiring is integrated in the garment such a solution is not practical since it would require the user to change the necessary connections between the stimulator and the electrodes thus introducing the opportunity for error.

According to a first aspect of the present invention there is provided apparatus for applying an electrical current to a neuromuscular system comprising a garment adapted to cover a portion of a user's body, a stimulation device for generating a stimulating current connectable to at least one electrical contact on said garment, the garment being shaped to correspond with a particular anatomical feature to ensure accurate and repeatable positioning of the garment with respect to the particular neuromuscular area to be treated.

According to a second aspect of the present invention there is provided apparatus for receiving an electrical signal from a neuromuscular system comprising a garment adapted to cover a portion of a user's body, a receiving device connected to at least one electrical contact on said garment, the garment being shaped to correspond with a particular anatomical feature to ensure accurate and repeatable positioning of the garment with respect to the particular neuromuscular area to be monitored.

Preferably, the garment is marked with one or more reference lines to aid the accurate and repeatable positioning of the garment with respect to a particular neuromuscular area.

Preferably, the neuromuscular area is the quadriceps muscle and the anatomical feature is the patella.

Preferably, the stimulation device is adapted such that it is interactable with the garment to determine whether it is a left-limb or right-limb garment.

Preferably, the garment has an arcuate shaped edge at its distal end to correspond with the top of the patella.

Preferably, the reference line is alignable with a notional line extending upwardly from the centre of the patella.

Preferably, the garment consists of an undergarment and an over-garment, the undergarment having at least one electrical contact on its skin-facing surface conductively connected to one or more corresponding electrical contacts on its opposite surface which, in turn, are conductively connected to contacts on the over-garment.

Preferably, the electrical connections between the undergarment and over-garment are made by stud fasteners which are fixed on and extend through the undergarment.

Preferably, a plurality of electrical contacts are provided on the undergarment.

Preferably, the or each electrical contact on the undergarment is conductively connectable to one or more skin engaging electrodes.

Preferably, the or each skin engaging electrode is user replaceable.

Preferably, four skin engaging electrodes are employed.

Preferably, at least one skin engaging electrode has a different surface area from the other skin engaging electrodes.

Preferably, the combined surface area of the electrodes is at least 300 $cm^2$.

Preferably, the electrode having the greatest surface area extends across the upper quadriceps.

Preferably, at least one of the remaining electrodes covers at least part of the lower fibres of the vastus medialis.

Preferably, at least one of the remaining electrodes covers at least part of the lateral fibres of the quadriceps.

Preferably, one of the skin engaging electrodes is generally dog-leg shaped.

Preferably, at least one of the skin engaging electrodes is generally rectangular in shape.

Preferably, printed outlines of the skin engaging electrodes are provided on the skin-facing surface of the undergarment to aid accurate positioning of the electrodes by the user.

Preferably, the skin engaging electrodes are displaced circumferentially to establish current pathways which transect the neuromuscular area.

Preferably, the stimulation device includes control means for selectively directing a stimulating current to one or more of the skin engaging electrodes.

Preferably, the control means includes user programmable software for controlling the duration of the stimulating pulses and their sequencing between the skin engaging electrodes.

Preferably, the control means includes user programmable software for selecting any subset or all of the skin engaging electrodes in the garment to form one electrical pole and any other subset or all of the remaining skin engaging electrodes in the garment as the opposite electrical pole.

Preferably, the control means includes user programmable software which allows the user to map control buttons on the garment such that current applied to the medial and lateral quadriceps muscles is controllable by medial and lateral control buttons respectively.

Preferably, the or each contact on the over-garment is conductively connected to the stimulation device of the first aspect.

Alternatively, the or each contact on the over-garment is conductively connected to the receiving device of the second aspect.

Preferably, the garment is securable to a user's body by hook and loop fasteners.

Preferably, the garment is configurable for use on the left or right leg.

Preferably, the connections between the stimulation device and the at least one electrical contact on said garment are preset and non-alterable by the user.

Preferably, the connections between the stimulation device and the at least one electrical contact on said garment are non-alterable by the user by virtue of the fact that they are integrated within the garment itself.

An embodiment of the present invention will now be described, by way of example only, with reference to the following drawings, wherein.

Figure 1:
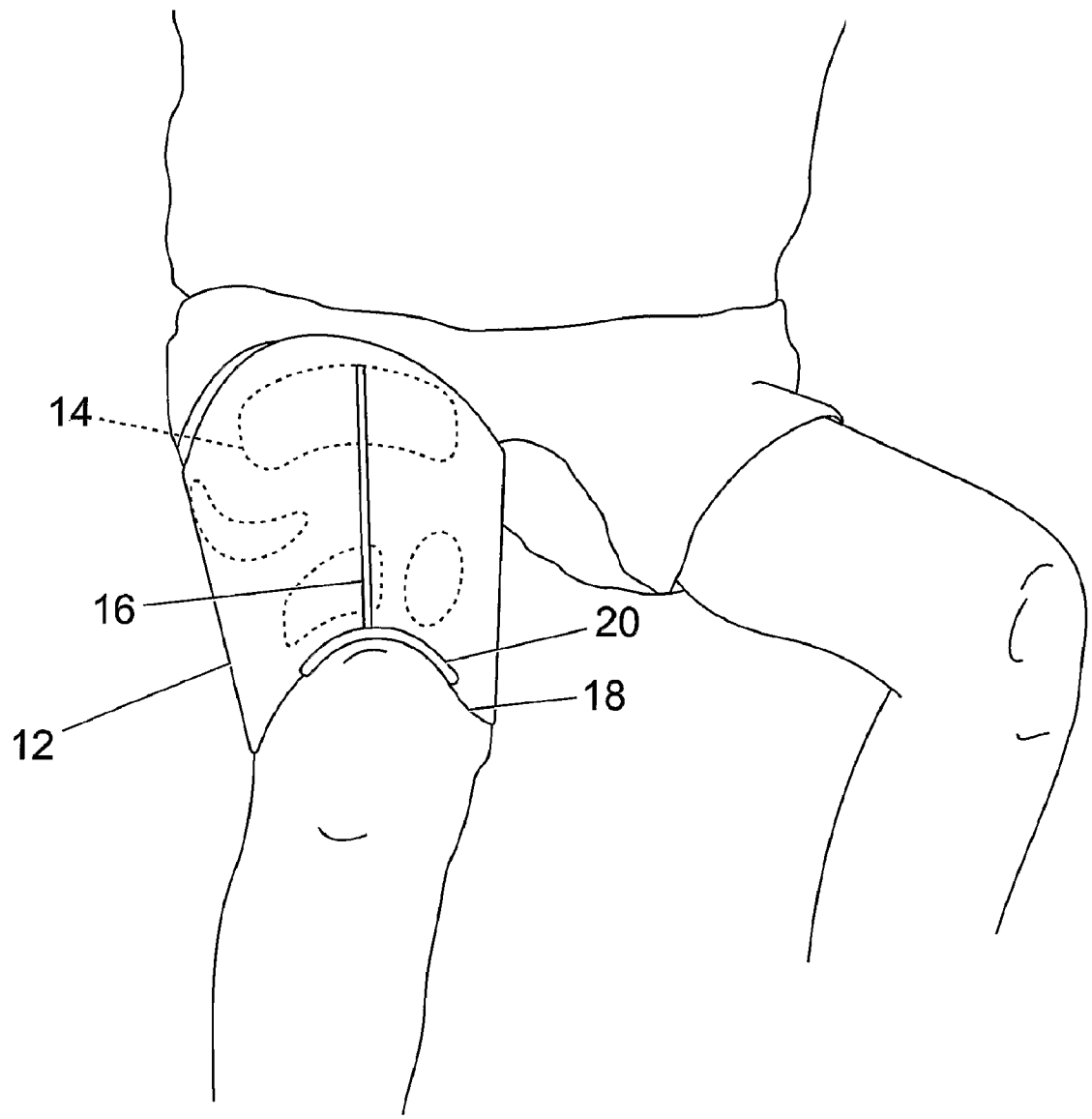
FIG. 1 shows apparatus for applying current to the quadriceps (undergarment and over-garment)

FIG. 1 shows apparatus for applying an electrical current to a neuromuscular system, said system being the quadriceps muscle, comprising an undergarment 12 provided with reference lines 14 and 16 respectively. A distal end 18 of the undergarment is provided with an arcuate shaped portion 20.

The term neuromuscular is to be understood to include muscles, muscle parts, muscle groups, nerves or a combination thereof.

The apparatus therefore locates unambiguously with an appropriate anatomical landmark. The anatomical locating means and corresponding anatomical landmark must be selected such that the variation in displacement of electrode positions with respect to the anatomical location means is minimised for individuals of different size. This allows a common design to be used by different individuals with minimal adjustment.

Typically, a useful anatomical reference is provided by a "bony" reference point on the body where the muscle position with respect to such a reference point is consistent between individuals. According to the present invention, the muscle and bony reference point is the quadriceps and the patella respectively. The patella is a sesamoid bone of the quadriceps muscle and so, by effectively being part of this muscle, it has a direct relationship to its movement. Regardless of the size of the patient, the lower fibres of the quadriceps insert via the quadriceps tendon and then into the patella. The lower lateral fibres insert just above and laterally with respect to the patella. The vastus medialis inserts a little lower on the medial side.

Accordingly, when designing a garment (see FIG. 1) to assist with quadriceps electrode placement it has been found that the following combination ensures correct location in two axes: (i) an anatomical locating means comprising an arcuate shaped edge 20 corresponding to the upper portion of the patella; and (ii) a reference line 16 through the mid point of the patellar curve and along the midline of the thigh.

It will be appreciated by those skilled in the art that the fitting of undergarment 12 to the leg and positioning it with the aid of the reference line 16 and the arcuate shaped portion 20 can be performed by the user without any professional assistance.

Figure 2:
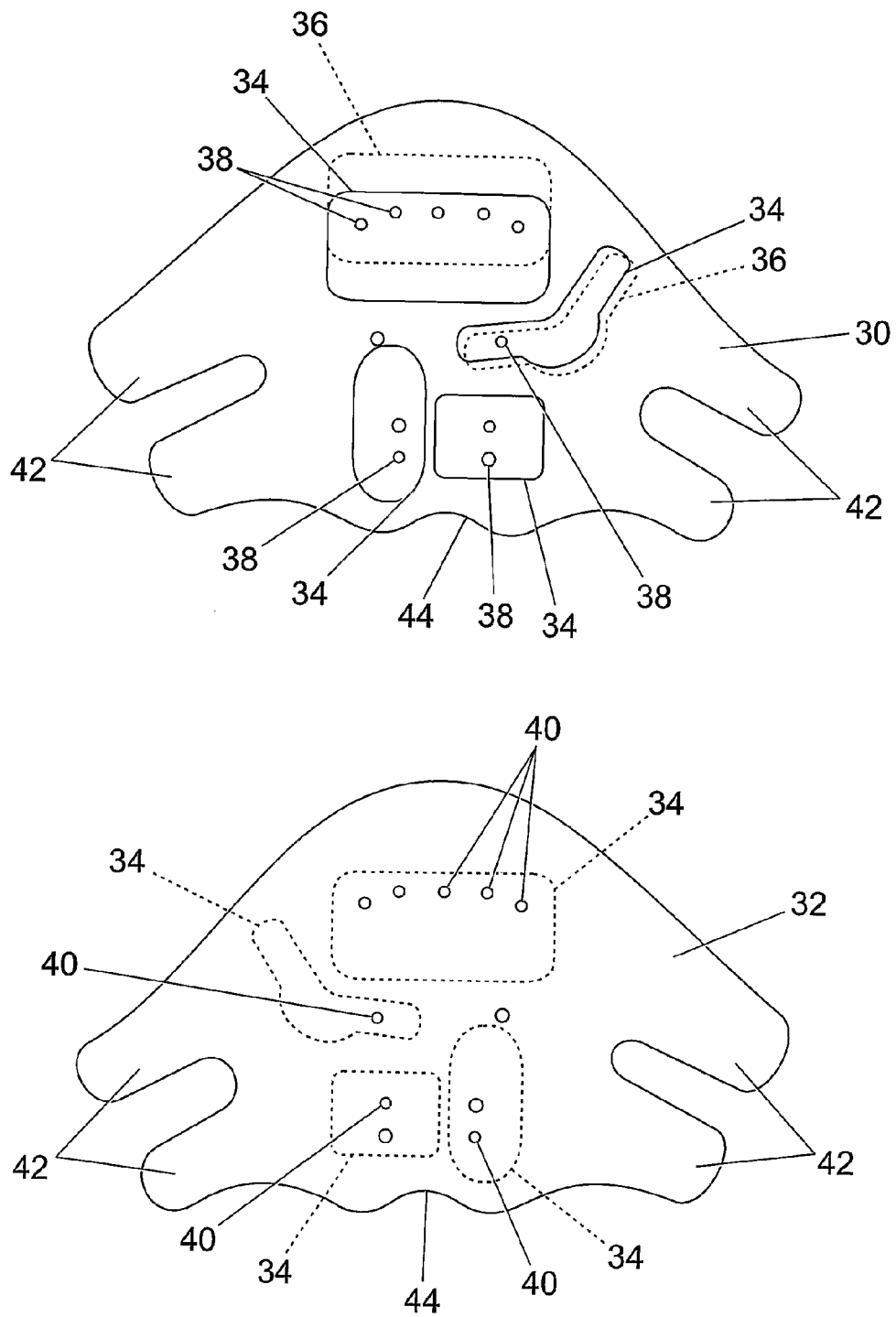
FIG. 2 shows the inner and outer surfaces of the undergarment.

FIG. 2 shows both the inner (skin facing) surface 30 and outer surface 32 of an undergarment adapted for use on the right leg. Reference lines 34 are provided on the inner surface 30 corresponding to the shapes of replaceable electrodes A, B, C and D for contacting the skin (discussed further below with reference to FIG. 4). Alternative reference lines 36 are also provided on the inner surface 30. The reference lines 34 are not intended to be visible on the outer surface 32 but are shown in FIG. 2 as dashed lines 34 for clarity.

Electrical contacts 38 are provided on the inner surface 30 of the undergarment and are conductively connected to corresponding electrical contacts 40 on the outer surface 32.

Velcro® straps 42 (i.e. hook and loop fasteners) are provided on either side of the undergarment and an arcuate shaped portion 44 (corresponding to reference numeral 20 in FIG. 1) is provided at its lower end.

In use, replaceable electrodes for contacting a user's skin are positioned on the skin facing surface of the undergarment with the aid of the reference lines 34. For some users (i.e. because of their size of other specific requirements) replaceable electrodes A and D are positioned to correspond with the alternative reference lines 36.

The undergarment is then fitted to the user's leg by wrapping and securing the Velcro® straps 42 around the thigh and aligning the arcuate shaped portion 44 with the top of the patella. The electrical contacts 38 on the inner surface 30 therefore make electrical contact with the replaceable electrodes which in turn contact the user's skin over the quadriceps muscle. The replaceable electrodes electrically connect to the contacts 38 by means of mating contacts or a conductive adhesive layer.

The contacts 38 are electrically connected to contacts 40 on the outer surface 32 of the undergarment. The electrical contacts 38 and 40 preferably comprise conductive stud fasteners which are fixed on and extend through the fabric of the undergarment. The flat surface of the stud fastener presents on the inner surface 30 whereas a male or female part of the stud fastener presents on the outer surface 32.

The reference lines 34 and 36 and the electrical contacts 38 are positioned to correspond with anatomical features such that upon correct application and alignment of the garment to the leg, electrodes of appropriate size, shape, orientation and electrical connection are positioned on the leg.

Figure 3:
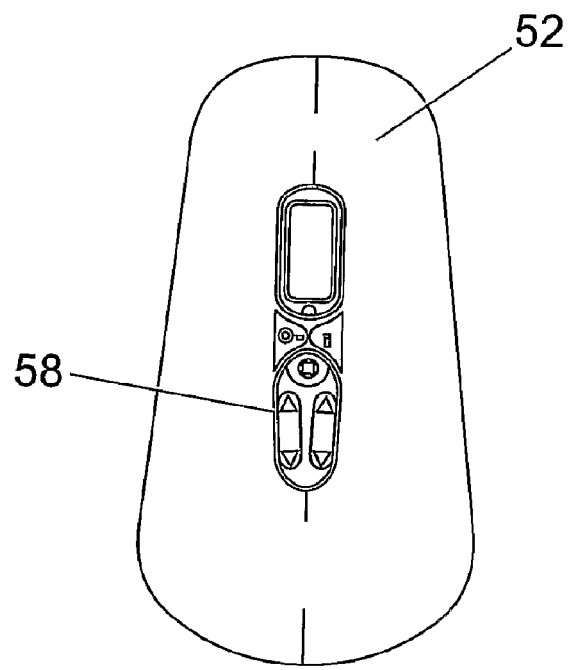
FIG. 3 shows the inner and outer surfaces of the over-garment.
Figure 3:
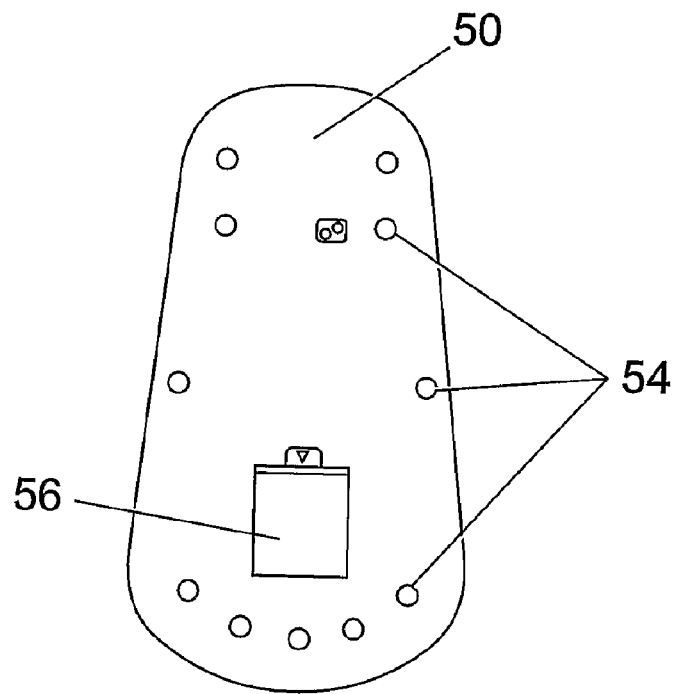

FIG. 3 shows both the inner surface 50 and outer surface 52 of an over-garment which is worn over the undergarment of FIGS. 1 and 2. The inner surface 50 is provided with stud fasteners 54 which are electrically connected to a stimulation device 56. Control means 58 for controlling the stimulation device are provided on the outer surface 52 of the over-garment.

In use, the over-garment is attached to the undergarment via their respective stud fasteners 54 and 40. A conductive path is thereby formed between the stimulation device 56 and the replaceable electrodes on a user's skin.

The over-garment is a flexible fabric envelope containing the stimulator electronics and a battery. The control means 58 comprises an integral Liquid Crystal Display (LCD) and button control panel located on the outer surface 52 of the over-garment. The user controls include two up and down controls for medial and lateral muscles. The stimulator internally re-maps these controls depending on whether it is operating on a left or right undergarment. For example, on a left undergarment, the rightmost amplitude control sets the intensity of the medial muscle, whereas on the right undergarment it is the leftmost amplitude control which sets the intensity of the medial muscle. This is particularly important when the sequencing of the muscle activation is required to recruit medial before lateral muscles.

Figure 4:
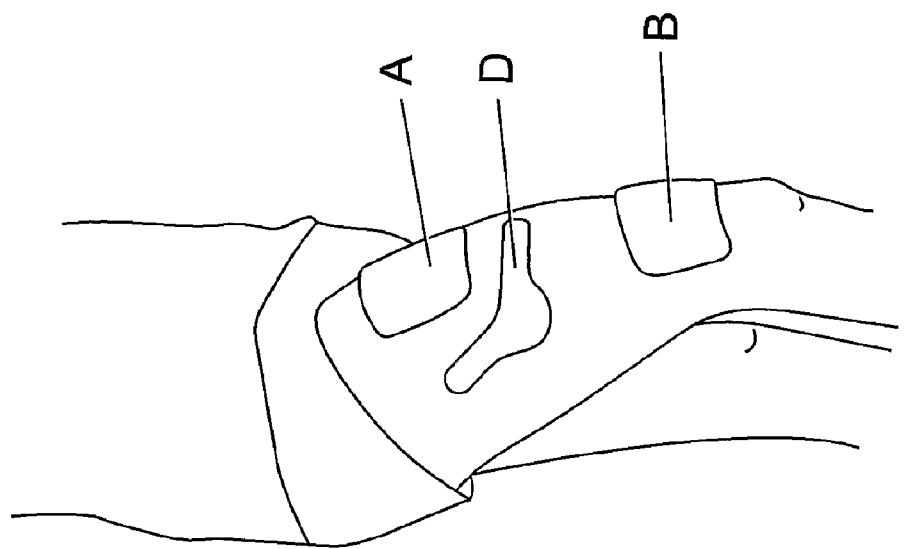
FIG. 4 shows the positioning of replaceable electrodes on the leg.
Figure 4:
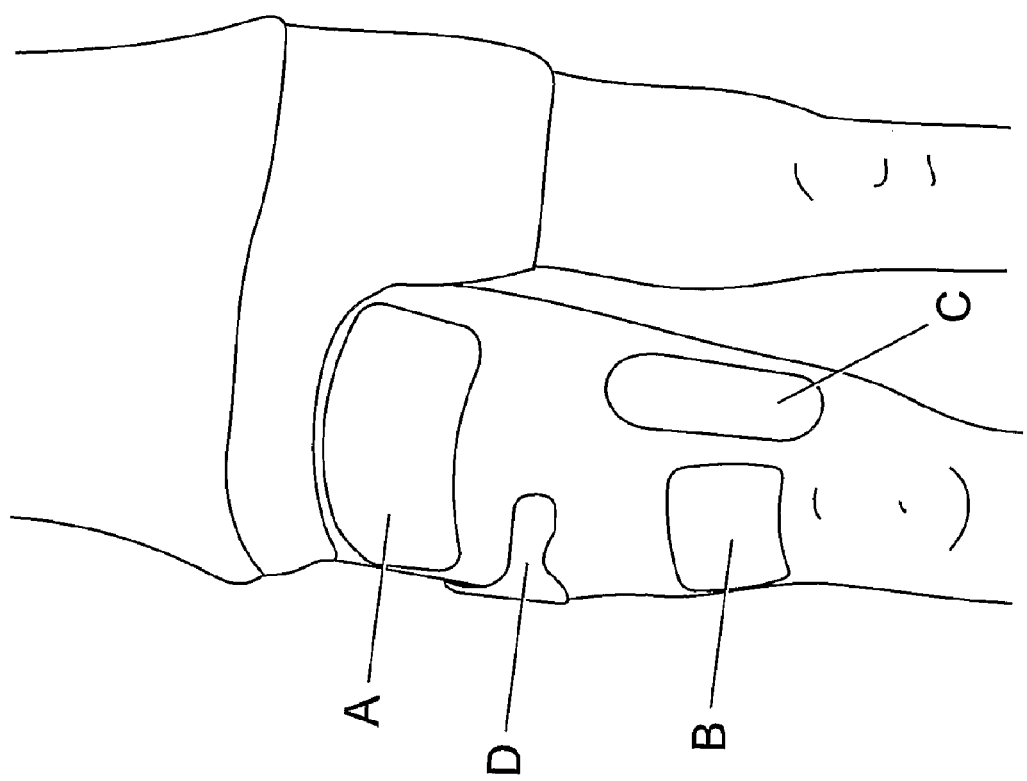

FIG. 4 shows four replaceable electrodes A, B, C and D which are positionable within the undergarment and, in use, contact the user's skin. This figure illustrates where each electrode typically locates on the right leg when the undergarment is applied in accordance with the user instructions. Electrode A covers the upper quadriceps area while electrodes B and C together cover the lower quadriceps area. Electrode C locates medially while B locates more centrally and extends laterally. Electrode D has a dog-leg shape and is positioned to recruit the more lateral fibres of the quadriceps.

Electrode A: This is a large electrode in the shape of a rectangle measuring 20 cm×10 cm (with rounded corners) positioned so as to extend across the upper quadriceps as illustrated. The electrode extends equidistant either side of the mid-thigh location mark and its lower edge is displaced 20 cm from the midpoint of the patellar locating arcuate portion described previously. An alternative position for electrode A is also provided to accommodate taller users which is 22 cm from the patellar mark. This electrode has a surface area of approximately 196 cm$^2$.

Electrode B: This electrode is in the shape of a rectangle measuring 10 cm×7.5 cm (again with rounded corners) positioned so as to extend across the lateral portion of the quadriceps muscle close to the patella. The major midline of this electrode is 7 cm from the patellar mark while the minor midline is displaced 4 cm laterally from the midline locating mark on the garment. This electrode has a surface area of approximately 74 cm$^2$.

Electrode C: This electrode is in the shape of a rectangle measuring 14 cm×6.5 cm (again with rounded corners) which extends along the medial portion of the quadriceps muscle close to the patella. The major mid line of the electrode is displaced 6 cm from the midline locating mark on the garment and the minor midline of the electrode is displaced 7 cm from the patellar locating edge. This electrode has a surface area of approximately 82 cm$^2$.

Electrode D: This is a small electrode which locates laterally on the upper leg. It is preferably dog-leg in shape and can be used on either the right or left leg. This electrode has a surface area of approximately 57 cm$^2$. An alternative, more lateral, position for the electrode is provided on the garment to accommodate thighs of larger girth.

In this non-limiting example, the total area of all four electrodes is approximately 410 cm$^2$. However, it will be appreciated that dimensions of the electrodes can be varied and are typically greater than 300 cm$^2$. The electrodes are as large as possible to recruit the target muscle with the minimum current density at the skin. It is clear that most of the anterior surface of the thigh is covered by one or other of the electrodes and this is very different to the established practice which favours much smaller electrodes which require more accurate placement. Using these much larger surface area electrodes has proved successful in recruiting the maximum number of muscle fibres whilst minimising current density at the skin.

The relative sizes and positions of electrodes when in place on the body define the current pathways which can be created. When electrodes are placed on a planar body surface then the penetration of the electric field is not as good as when electrodes are placed on a curved surface. By choosing electrode positions which establish current pathways which transect the body structure then stimulation of deeper tissue can be achieved. The thigh, in simple terms, is a cylindrical formation with little curvature along its length but high curvature around its circumference. Accordingly, by positioning one electrode displaced circumferentially from another electrode located at the anterior thigh midline we achieve deeper penetration. The appropriate dimensioning of this displacement with respect to relevant anatomical markers ensures that selected nerves are stimulated.

The preferred positioning of the replaceable electrodes is as follows. One large electrode covering the upper fibres of the quadriceps and the femoral nerve and (its upper branches). Two lower electrodes cover the distal quadriceps fibres. The inner lower electrode is sized and shaped so that it covers the lower fibres of the vastus medialis. This gives us the option to zone in on this muscle separately for part of the rehabilitation. The fourth electrode is an outer lateral electrode and lies on the extreme lateral fibres of the quadriceps and its main function is to direct the impulses from the combination of electrodes in a different direction. This electrode is displaced circumferentially from the anterior thigh midline and when used in conjunction with some or all of the other electrodes creates current paths with transect the thigh thereby stimulating deeper tissue. This allows rehabilitation of a greater variety of fibres within the muscle.

The large surface areas of these electrodes allow for a more comfortable contraction, because the skin current density is reduced. Furthermore, this reduces the necessity for precise adjustment of electrode positioning between individuals.

Figure 5:
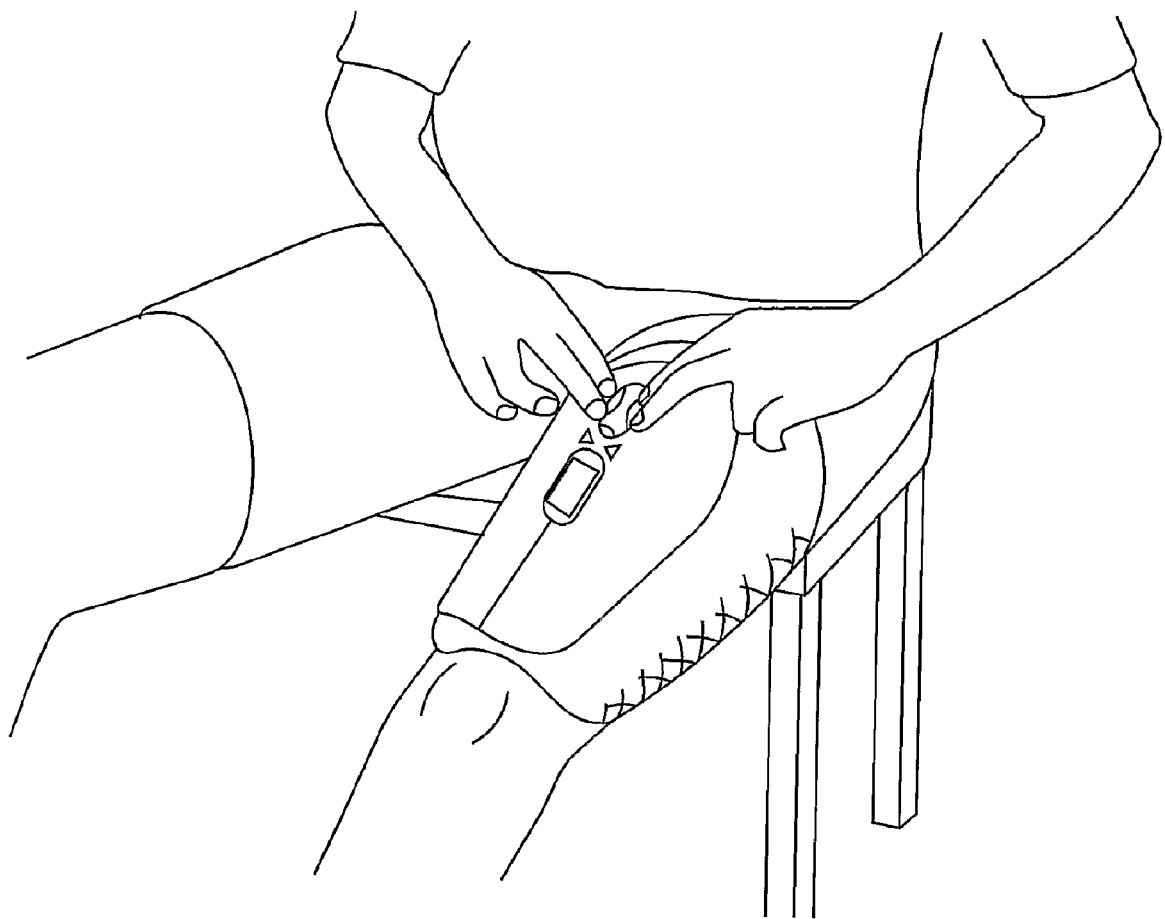
FIG. 5 shows the apparatus in use.

FIG. 5 shows the apparatus in use whereby the user can control the stimulation of the quadriceps muscle.

The apparatus comprises an over-garment having an integrated stimulation device which includes integrated electronics, an LCD display, user controls and a battery. The integrated nature of the electrical connections means that the user does not have to make individual connections between the stimulator terminal and each replaceable electrode. Apart from removing the requirement to select electrical connections, such a system can automatically change between left leg and right leg modes by transposing connections and the mapping of user controls and display elements.

While the apparatus may work with a simple single or dual channel stimulator, it is preferable that the apparatus is connected to an advanced stimulator, as more fully explained below. This allows the selection of any subset of electrodes as one electrical pole (i.e. as a cathode) and any other subset as the other electrical pole (i.e. as an anode) and therefore creates a choice of current pathways through the thigh.

The success of traditional Electrical Muscle Stimulation (EMS) systems depend on the relative positions of the array electrodes on the body, and the correct connection to signal sources in the stimulator. Any errors could lead to a completely different current path in the body from that intended. For this reason these techniques are not suitable for general use with traditional exposed leadwire systems which are prone to human error.

The present apparatus solves this problem by providing an electrode locating means, and an electrode connection means within an integrated tamperproof garment. The electrode selections and the timing thereof are as follows.

The preferred apparatus has an integrated two-channel electronic muscle stimulation garment operating with four replaceable skin electrodes. Preferably, the stimulation signal takes the form of a modulated pulse train, utilising a symmetric biphasic pulse with interphase interval, operating under constant current control. Each stimulation pulse may be divided into a number of time segments, called timeslots, and different electrode selections can be made under software control for each timeslot.

The general effect of this approach is to achieve larger effective electrode areas by combining the areas of individual electrodes. This reduces skin current density for a given stimulation current level. The effect of dividing the pulse into timeslots with different electrode selections is to vary the phase charge seen by each electrode and therefore the intensity of stimulation associated with each electrode.

Where electrodes are combined to form an anode or cathode, then the current density at the skin is reduced, thereby reducing skin sensation compared to the situation of using only one of the electrodes.

Circuits comprising an anode set and a cathode set can be created whereby the anode and cathode have unequal areas. The current density for the lower area group is therefore higher than for the high area group.

Where electrodes are combined to form an anode or cathode, then the spatial distribution of the current in the quadriceps area is changed because of the dispersion of the current over the larger electrode area.

The apparatus operates with predetermined electrodes with a defined design area and shape. Therefore the current densities and current distributions between the electrodes are controlled and cannot be changed by the user. At worst case, the user could apply the wrong size or shape electrode in the wrong position on the undergarment. In this worst case, the maximum current density still cannot exceed the design limit although the effectiveness of the stimulation would possibly be reduced. A user cannot change the connections to the electrodes or alter the sequencing of the stimulation signals applied to the electrodes. The opportunities for error are therefore greatly reduced.

Figure 6:
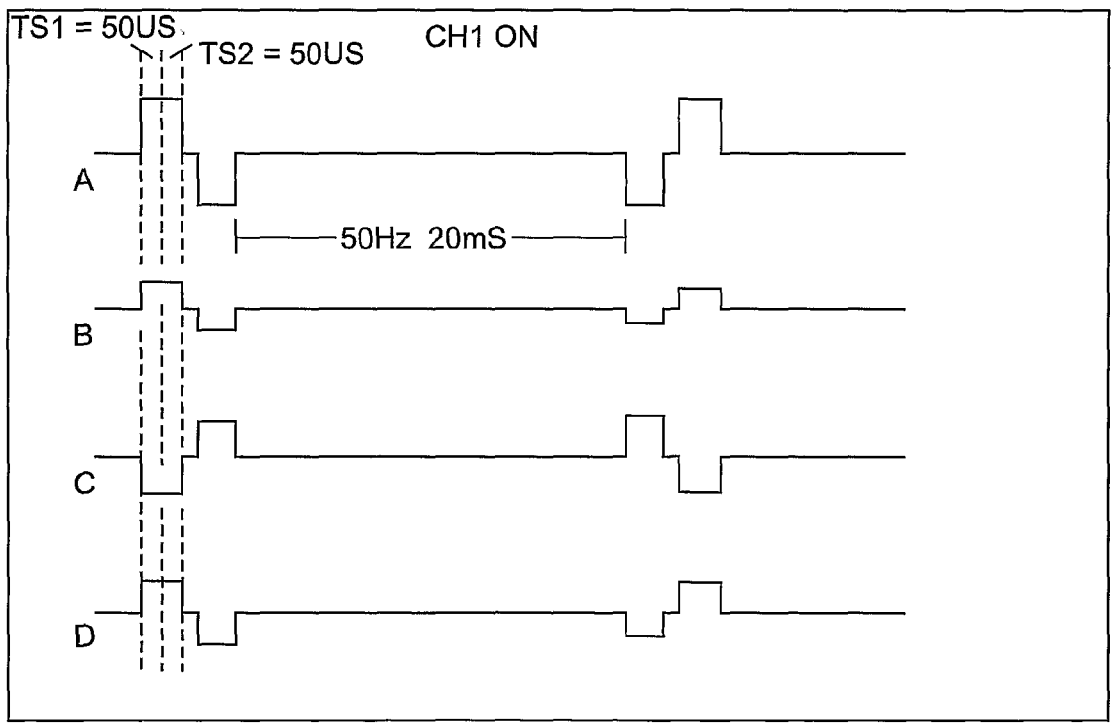
FIG. 6 shows the electrode sequencing of the apparatus.

Tables 1 and 2 in FIG. 6 show examples of electrode sequencing. "H" indicates the electrode sources current for the period, "L" indicates the electrode sinks, while "X" indicates the electrode is unused in the period.

In one example of the operation of the apparatus (see Table 1), Channel 1 has a stimulation pulse phase duration of 100 µS and a consistent electrode pattern is maintained throughout. Electrodes A, B and D are electronically combined together to form a single electrode while electrode C is selected as the opposite pole. This has the effect of reducing the current density in A, B and D compared to C, thereby increasing the relative stimulation of the medial quadriceps compared to the rest of the muscle group.

Meanwhile, Channel 2 has a pulse phase duration of 400 µS, which is divided into two timeslots, of 300 µS and 100 µS respectively. The electrode selection pattern for the first timeslot groups electrodes B and C together as a single electrode with electrode A as the opposite pole electrode. Electrode D is unconnected for the first timeslot. This selection effectively creates a single large electrode at the lower quadriceps operating with the single large electrode A at the upper quadriceps. For the second timeslot only, electrodes A and D are selected. This directs a stimulation signal to the lateral D electrode, increasing the lateral recruitment to the muscle contraction. Channel 2 therefore stimulates the quadriceps in general, with a bias towards the lateral components of the muscle.

The electrode drive patterns for channel 1 and channel 2 are automatically changed by software such that channel 1 is operable by the left hand amplitude controls when fitted on a right leg undergarment, and by the right hand amplitude control when fitted on a left leg undergarment. In this way, the medial part of the muscle is always operable by the medial amplitude control, whereas the lateral muscle group is always operable by the lateral amplitude control.

A further example of electrode sequencing together with the current patterns at each electrode is provided in the second table in FIG. 6 with the corresponding current patterns for each electrode shown underneath. (The current patterns are not to scale in either time or current amplitude)

Various modifications and improvements may be made without departing from the scope of the present invention.

For example, an alternative to the arcuate shaped portion which corresponds with the shape of the patella could be a donut shaped locator at the distal end of the undergarment. However this design, as with any thigh garment with a knee splint, would tend to pull on the undergarment proximally when the knee joint flexes.

Two versions of the undergarment could be provided, one for the right and one for the left leg. An identical array of stud fasteners would be provided on either type however a different subset of contacts would be used for the left and right versions. An undergarment would be factory configured for left or right use by electrically linking one stud fastener in one of two alternative positions. This would allow the stimulator electronics to detect which undergarment is connected and thereby direct the appropriate signals to each element of the stud array. Alternatively, unused stud fasteners could be insulated with an insulating cover.

While the preferred apparatus includes the over-garment having an integrated stimulator device, it could be adapted for use with various conventional electrical stimulation units. A simple single or dual channel stimulator device could be connected to the appropriate electrodes using, for example, leadwires terminating in stud faster contacts. For general quadriceps rehabilitation both channels would be used.

In the case where a clinician needs to zone in on extra rehabilitation of the vastus medialis the medial channel is used alone. When both channels are used there is a default feature that brings in the contraction of the vastus medialis before the rest of the bulk of the quadriceps. This is particularly useful for the person with an unstable patella. If the patella is prone to dislocation it will invariably be in the lateral direction. In this embodiment the patella is pulled slightly inwards and then upwards, ensuring stability of the patella.

While the electrode configuration described has several advantages it is also possible to use smaller electrodes of conventional round and/or rectangular shape. Accurate location of such electrodes can still be achieved by a suitable garment which includes the anatomical reference means described (i.e. the patellar location arcuate portion). The apparatus may include at least one electrode and may include an array of electrodes which will all locate correctly if referenced to the locating means.

Any form of electrical therapy or biological signal detection could be applied to this garment such as TENS, EMG etc. Indeed, a combined dual function stimulation and receiving device could be incorporated into the garment (i.e. a combination of the first and second aspects of the invention).

Garments for other muscle groups in the body could also be included provided there was a fixed relationship between the locating surface anatomical feature and the intended muscle, muscle group or nerve to this group. Examples of this may include the reliable location of the common peroneal nerve just below the fibular head or the ulnar nerve behind the medial condyle of the humerus. There can also be a specific relationship between anatomical features and the movements of a muscle whether it displaces with movement or simply shortens in an isometric contraction.

The invention claimed is:

1. Muscle stimulation apparatus for applying an electrical current to the leg muscles comprising:
    a garment adapted to cover an upper area and a lower area of the quadriceps;
    a stimulation device for generating a muscle stimulating current in the form of a pulse train connectable to at least three fixed electrical contacts on said garment, the garment being shaped to correspond, in use, with a particular anatomical feature on a user to ensure accurate and repeatable positioning of the garment with respect to the upper and lower areas of the quadriceps muscles to be treated such that one fixed electrical contact covers upper fibres of the quadriceps and two fixed electrical contacts cover lower fibres of the quadriceps close to the patella; the stimulation device further comprising control means for selectively directing stimulating pulses between said three or more fixed electrical contacts, and wherein different fixed electrical contact selections can be made under software control for selecting any subset of the fixed electrical contacts in the garment to form one electrical pole, and any other subset or all of the remaining fixed electrical contacts in the garment as the opposite electrical pole so as to create pulse sequences comprising stimulating pulses capable of being directed through six different pathways between three of said fixed electrical contacts.

2. Apparatus according to claim 1 wherein the garment is marked with one or more reference lines to aid the accurate and repeatable positioning of the garment with respect to the quadriceps.

3. Apparatus according to claim 1 wherein the stimulation device is adapted such that it is interactable with the garment to determine whether it is a left-leg or right-leg garment.

4. Apparatus according to claim 1 wherein the garment has an arcuate shaped edge at its distal end to correspond with the top of the patella.

5. Apparatus according to claim 2 wherein at least one reference line is alignable with a notional line extending upwardly from the centre of the patella.

6. Apparatus according to claim 1 wherein the garment consists of an undergarment and an over-garment, the undergarment having at least three fixed electrical contacts on its skin-facing surface conductively connected to corresponding fixed electrical contacts on its opposite surface which, in turn, are conductively connected to contacts on the over-garment.

7. Apparatus according to claim 6 wherein, stud fasteners which are fixed on and extend through the undergarment provide electrical connections between the undergarment and the over-garment.

8. Apparatus according to claim 1 wherein the fixed electrical contacts are displaced circumferentially to establish current pathways which transect the neuromuscular area.

9. Apparatus according to claim 1 wherein the control means includes user programmable software for controlling the duration of the stimulating pulses and their sequencing between the fixed electrical contacts.

10. Apparatus according to claim 1 wherein the control means includes user programmable software which allows the user to map control buttons on the garment such that current applied to a medial and a lateral quadriceps muscle is controllable by a medial and a lateral control button respectively.

11. Apparatus according to claim 1 wherein the connections between the stimulation device and the plurality of fixed electrical contacts on said garment are preset and non-alterable by the user.

12. Apparatus according to claim 11 wherein the connections between the stimulation device and the plurality of fixed electrical contacts on said garment are integrated within the garment itself.

13. Apparatus according to claim 1 wherein each stimulation pulse is divisible into a number of timeslots and different fixed electrical contact selections can be made under software control for each timeslot.

14. Apparatus according to claim 6 wherein each fixed electrical contact on the undergarment is conductively connectable to a skin engaging electrode.

15. Apparatus according to claim 14 wherein four fixed electrical contacts are employed.

16. Apparatus according to claim 14 wherein at least one fixed electrical contact has a different surface area from the other skin engaging electrodes.

17. Apparatus according to claim 14 wherein the combined surface area of the skin engaging electrodes is at least 300 cm$^2$.

18. Apparatus according to claim 16 wherein the skin engaging electrode having the greatest surface area extends across the upper quadriceps.

19. Apparatus according to claim 18 wherein, at least one of the remaining skin engaging electrodes covers at least part of the lower fibres of the vastus medialis.

20. Apparatus according to claim 18 wherein, at least one of the remaining skin engaging electrodes covers at least part of the lateral fibres of the quadriceps.

21. Apparatus according to claim 14 wherein one of the skin engaging contacts is generally dog-leg shaped.

22. Apparatus according to claim 14 wherein at least one of the skin engaging electrodes is generally rectangular in shape.

23. Apparatus according to claim 14 wherein, the skin-facing surface of the undergarment comprises reference lines corresponding to the shape of each skin engaging electrode to aid accurate positioning of the skin engaging electrodes by the user.

* * * * *